United States Patent [19]

Eckenhoff et al.

[11] Patent Number: 4,756,314

[45] Date of Patent: Jul. 12, 1988

[54] SWEAT COLLECTION PATCH

[75] Inventors: James B. Eckenhoff; Felix Theeuwes, both of Los Altos, Calif.

[73] Assignee: ALZA Corporation, Palo Alto, Calif.

[21] Appl. No.: 52,315

[22] Filed: May 21, 1987

Related U.S. Application Data

[63] Continuation of Ser. No. 792,082, Oct. 28, 1985, abandoned, which is a continuation of Ser. No. 529,776, Sep. 6, 1983, abandoned.

[51] Int. Cl.$^4$ ............................................. A61M 31/00
[52] U.S. Cl. .................................... 128/760; 128/766; 128/623
[58] Field of Search ..................... 128/623, 766, 760; 604/378

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes | 128/260 |
| 4,014,334 | 3/1977 | Theeuwes et al. | 128/260 |
| 4,077,407 | 3/1978 | Theeuwes et al. | 128/60 |
| 4,329,999 | 5/1982 | Phillips | 128/260 |

OTHER PUBLICATIONS

Heyer et al, "Effect of . . . Solutes . . . on Osmotic Flow", Yale Jrnl. Bio & Med., Dec.-Feb. 1970, pp. 139-153.

Peck et al, "Continuous Drug Collection", Jrnl. Pharm. & Biopham., vol. 9, No. 1, 1981, pp. 41-57.

Phillips et al, "Long-Term Sweat Collection", Jrnl. Inst. Derm., vol. 68, No. 4, 1977, pp. 221-224.

Phillips, "Improved Adhesive Patch", Bio. Mat. Med. Dev. Art Org., 81, pp. 13-21, 1980.

Boher, "Measurement of Water Loss", Arch. Derm.-vol. 96, 1967, pp. 441-452.

Primary Examiner—Edward M. Coven
Attorney, Agent, or Firm—Shelley G. Precivale; Edward L. Mandell; Steven F. Stone

[57] ABSTRACT

An improved fluid collection patch is disclosed which is capable of providing a quantitative indication of the average concentration of an agent in a body fluid during a collection period. The patch covers a predetermined area of a fluid secretory body surface such as the skin or mucous membrane and is provided with means for maintaining the flow of fluid into the patch substantially constant during the collection period. Preferred flow control means comprise an osmotic agent in the fluid flow path separated from the body surface by a semipermeable membrane. In a preferred embodiment the patch is adhesively bonded to the skin to collect sweat.

29 Claims, 2 Drawing Sheets

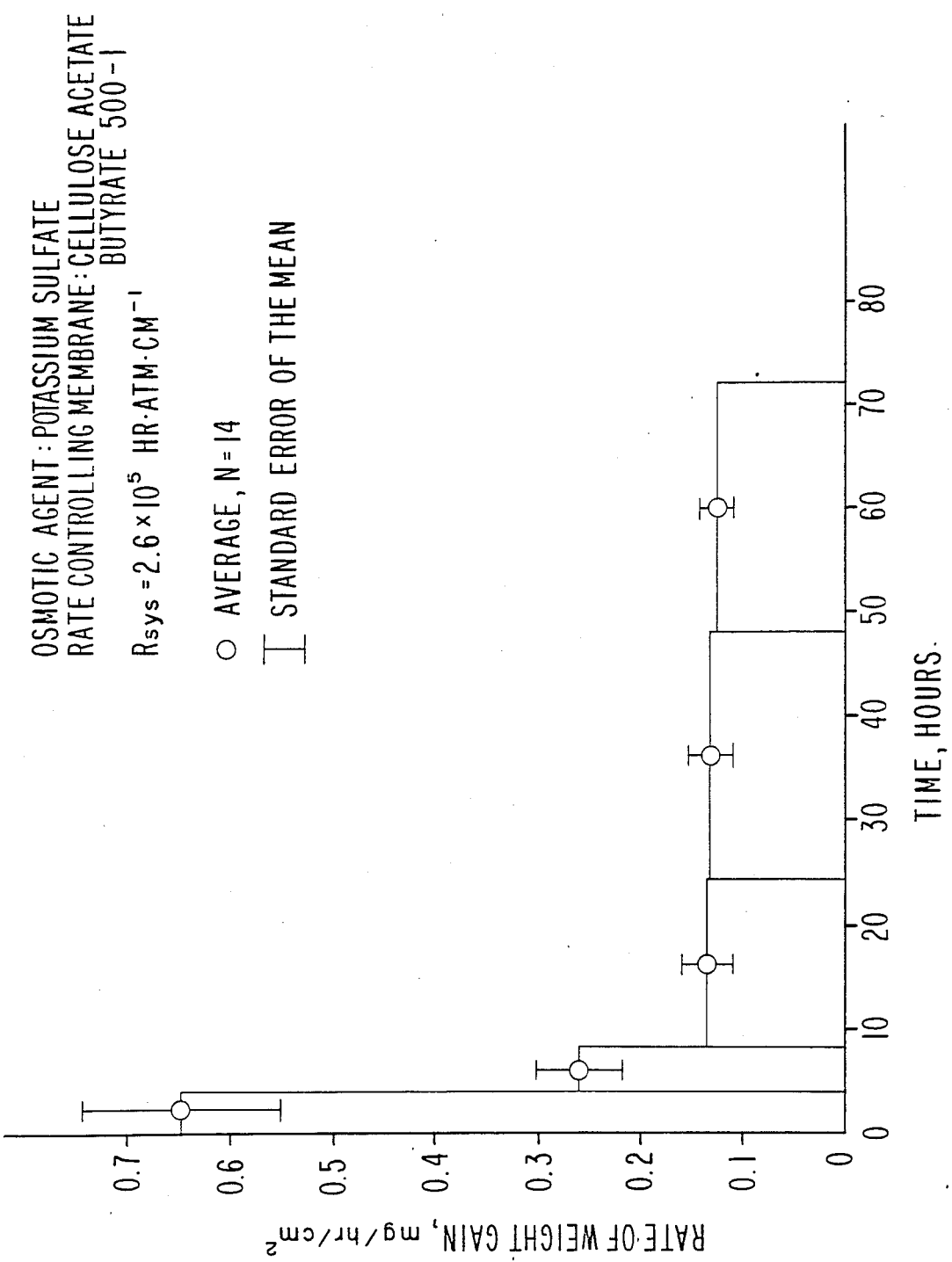

SWEAT COLLECTION PATCH

RELATED PATENT APPLICATIONS

This application is a continuation of Ser. No. 06/792,082 filed Oct. 28, 1985 now abandoned which is a continuation of Ser. No. 06/529,776 filed Sept. 6, 1983, now abandoned.

FIELD OF THE INVENTION

This invention relates to fluid collection patches useful in detecting the presence of drugs and other chemical compounds in the sweat, saliva or other secretory body fluid of the subjects from which the sample is obtained.

BACKGROUND OF THE INVENTION

It is known to the art that drugs such as alcohol, aminopyrine, antipyrine, methylurea, acetamide, sulfaguanidine, sulfadiazine, theophylline, and other low molecular weight nonelectrolytes are secreted through the skin or mucous membrane in sweat, saliva or the like. Other compounds which may be indicative of certain normal or disease conditions such as phenyalanine (phenylketonuria), sugar (diabetes), estriol (pregnancy), calcium (neoplasms) and copper (leukemia) for example, as well as normal and abnormal metabolites of other substances may be secreted in such fluids. Fluid collection is also used experimentally for determining biological requirements of various substances such as magnesium. If fluid samples are obtained and analyzed for these materials, the presence of such materials in the body can be detected. Such fluid collection therefore is useful in a wide variety of experimental, diagnostic, therapeutic and forensic medical purposes. While such fluids can be collected in numerous ways, a simple, easy to use technique utilizes an adhesive collection patch comprising a salt impregnated, fibrous, collecting pad which is mounted in an occlusive backing and adhered to the skin or mucous membrane of the mouth, vagina or other body cavity. The patch is removed after a predetermined time and analyzed for the presence of the chemical substance in question.

A typical patch is described in detail in Phillips, "An Improved Adhesive Patch for Long Term Collection of Sweat", Biomat., Med. Dev., Art. Org., 8(1), 13–21 (1980). While this patch yields, on an individual patch basis, a relatively constant uptake with time, there is a large variance in uptake, not only between individuals, but also between different patches on the same individual at the same site and between different patches on the same individual at different sites.

As can be seen from Baker, et al., "Measurement of Transepidermal Water Loss by Electrical Hygrometry", Arch. Derm., Vol. 96, pp. 441-452, Oct. 1967, water loss through the skin occurs through two independent processes, eccrine sweating and transepidermal diffusion. The volume of water loss through eccrine sweating is dependent upon many factors, such as ambient temperature, clothing, thermal stress, and level of exercise and can vary from a negligible amount to as much as 2 liters per hour under severe thermal stress. Transepidermal diffusion is a relatively steady passive process, the rate of which is dependent upon the ambient humidity, the skin surface temperature and the permeability of the skin to water loss. Water permeability of normal skin varies from site to site, from approximately 0.29 mg/hr.cm$^2$ on the back to as much as 1.14 mg/hr.cm$^2$ on the palm of the hand. In addition, variations in skin permeability are obtained as a result of any damage to the stratum corneum which is the major biological barrier to water loss in the skin. The damage can either be caused by injury, by intentional treatment with various materials such as hyperosmolar solutions, dimethyl sulfoxide, n-decylmethyl sulfoxide, dimethyl lauramide, ethanol, sodium lauryl sulphate or other materials known to have a permeation enhancing effect on the stratum corneum, or by stripping of the stratum corneum, such as occurs by the mere application and removal of an adhesive tape. The existing sweat collection patches, therefore, are capable of providing a qualitative indication of the presence or absence of a particular substance in the sweat during the collection period but are not capable of providing a quantitative indication of the average concentration of the agent during the sweat collection period. This is because they do not collect a constant volume of sweat per unit of time, independent of the aforementioned variables affecting the amount of sweat produced by the body in any particular time period at any particular body location and because they experience substantial back-diffusional losses.

According to our invention, however, we have devised a fluid collection patch in which the variation of collection rate between patches, between sites, and between individuals can be reduced or eliminated. Another advantage of the collection patches according to this invention is that the back-diffusion of fluid and therefore agent to be detected may be minimized, if not eliminated. By rendering the collection rate more uniform, constant and irreversible with time; quantitative analysis of the agent in the patch will yield a direct measurement of the average concentration of the agent in the fluid during the collection period.

For example, as Peck et al., have shown in the article, "Continuous Transepidermal Drug Collection: Basis for Use in Assessing Drug Intake and Pharmacokinetics." Journal of Pharm. and Biopharm. (9) 1, 1981, the amount of drug collected into a collection patch can be expressed by;

$$A_c(t) = \int_e \left( K_{1c} \left( \int A_1 dt \right) - K_{c1} A_c \right) dt$$

where $K_{1c}$ and $K_{c1}$ the transfer process rates between the drug source $A_1$ and the collection patch $A_c$. The term $K_{c1}A_c$ represents the back diffusion rate from $A_c$ to $A_1$. Collection patches accounting to our invention can eliminate this term so that the agent input rate into the collection patch is constant and reflects agent level in the fluid.

It is accordingly an object of this invention to provide an improved fluid collection patch.

It is another object of this invention to provide a fluid collection patch, the analysis of which will provide a time integrated average of the concentration of the agent in the fluid during the collection period.

It is another objection of this invention to provide an osmotically driven fluid collection patch with a semipermeable rate-controlling membrane.

It is another object of this invention to provide a fluid collection patch capable of collecting a constant volume of fluid per unit time during the collection period, independent of the volume of fluid produced per unit area of body surface.

It is another object of this invention to provide a collection patch capable of minimizing back diffusion of fluid and therefore agent to be detected.

It is another object of this invention to provide a fluid collection patch which protects the skin or mucous membrane from contact with hyperosmolar solutions.

These and other objects of this invention will be readily apparent from the following description with reference to the accompanying drawings, wherein:

FIG. 5 is a plot of weight gain vs. time for the embodiment of Example 1.

The following description relates primarily to sweat collection patches used by application on the skin of a subject. Nevertheless the same principles are applicable to patches adapted to collect fluid from other secretory body surfaces, such as the buccal membranes of the mouth and the vaginal or rectal mucous membranes, for example.

Figure 1:
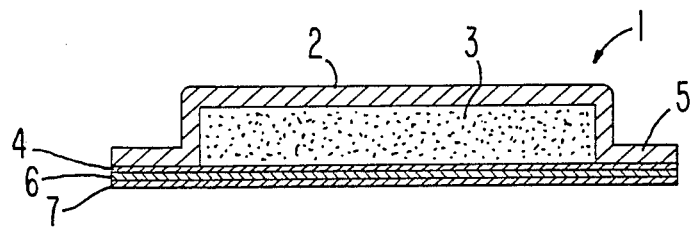
FIG. 1 is a cross-section through one embodiment of a fluid collection patch according to this invention.

Referring now to FIG. 1, a simple embodiment of this invention is shown which is useful in collecting sweat samples for the determination of the presence of low molecular weight substances such as alcohol, aminopyrine, antipyrine, methylurea, acetamide, sulfaguanidine, sulfadiziaine, theophylline and acetaldehyde for example. The collection patch 1 consists of a protective, preferably impermeable backing 2 formed into a receptacle which has received therein an absorbent pad 3 which is impregnated with an osmotically active material such as a highly soluble salt and which is sealed within the receptacle by means of semipermeable membrane 4 bonded to flange 5. The semipermeable membrane 4 is permeable to water and the agent to be collected and impermeable to the osmotically active material.

In operation, sweat containing dissolved agent is osmotically imbibed across the semipermeable membrane into the receptacle in direct relation to the osmotic pressure gradient across the semipermeable membrane and the permeability of the membrane. The volume rate of imbibition is constant as long as the concentration of the osmagent solution formed within receptacle is maintained at saturation and the temperature is maintained relatively constant. Collection patches of different duration and sweat collection rates can be designed by varying the osmotic agents and/or permeability of the membranes by techniques described below.

Any of a wide variety of natural and synthetic semipermeable membranes are known to the art as osmotic or reverse osmotic membranes and the particular membrane selected is not critical to this invention. Suitable materials are ennumerated in detail in U.S. Pat. Nos. 3,845,770, and 3,916,899, 4,077,407, and 4,014,334, all of which are incorporated herein by reference.

At least the peripheral portion 5 of the patch 1 or the entire undersurface of patch 1, as shown, is provided with a contact adhesive 6 which is permeable to water and the substance to be collected and a strippable impermeable liner 7 is applied to protect patch 1 prior to use. In use, the strippable liner 7 would be removed and patch 1 applied to the surface of the skin such as shown on the forearm 8 in FIG. 2.

Although adhesive means for maintaining the patch in good fluid conducting relationship to the skin are preferred, other means such as adhesive overlays, belts, Velcro ® fasteners or elastic bands, for example, can be used.

The absorbent pad 3 has dispersed therethrough sufficient undissolved osmotic agent such that the concentration of the solution formed within the collection pad as a result of the imbibition of water through the semipermeable membrane 4 will be maintained at the saturation level throughout the intended sampling period. In addition, the collection pad may also contain dispersed therethrough a collecting material such as colloidal silica, ion exchange resins, activated charcoal or other materials that selectively adhere to the agent to be detected to prevent back diffusion of the agent through the membrane 4.

The osmotic agent can be selected from any of a wide variety of soluble materials having a high osmotic pressure such as those described in the aforementioned U.S. patents which were incorporated by reference. Typical of such agents are sodium chloride, potassium chloride, potassium sulfate, pectin, and sorbitol for example. Any of these materials can be used since the concentration of material in the solution behind the semipermeable membrane will be maintained at saturation and the osmotic pressure of these materials at their saturation concentration will be substantially greater than the osmotic pressures generated by sweat or by typical concentrations of agents to be detected in the sweat. The osmotic pressure differential across the rate-controlling membrane will therefore be substantially invariant.

Membrane 4 is fabricated such that the water transmission through the membrane 4 is no greater than, and preferably lower than, the rate at which water diffuses from the skin at the site upon which the sweat collection patch is superposed. Thus for example, if the patch is intended to be applied to the forearm, Table 3 of the aforementioned Baker, et al. article indicates that the mean water loss of this area of the body is approximately $0.31 \pm 0.06$ mg/hr cm$^2$. In this case, therefore, one could select the semipermeable membrane such that it transmits 0.20 mg/hr.cm$^2$ or less of water such that there will be an adequate safety factor to establish that the rate of water influx into the collecting pad is established by the system (i.e., system controlled) rather than by the rate at which the sweat is produced by the body at the site of application. The skin at the collection site can also be pretreated by abrasion or stripping as described in Baker or by application of a permeation enhancer to increase the flow of sweat. With such pretreatment membrane 4 could be selected to pass water at a higher rate.

The volumetric flow rate through a semipermeable membrane in any osmotic system is directly proportional to the area of the membrane and the osmotic pressure differential existing across the membrane and inversely proportional to the thickness of the membrane according to the following relationship:

$$\frac{dv}{dt} = K \frac{A\pi}{h} \quad (1)$$

wherein v is the volume of fluid in cm³, t is time in hours, A is the area of the semipermeable membrane in cm², π is the osmotic pressure differential in atmospheres, h is the thickness of the membrane in cm and K is the permeability of the membrane to the fluid expressed in units cm²/hr atm. The value of K for any particular material is either known to the art or can be readily determined by standard experimental techniques will established in the art, such as are disclosed in J. App. Poly. Sci. Vol 9, pp. 1341-1362 (1965) and Yale J. Bio. Med., Vol 42, pp. 139-153 (1970).

According to this invention the permeability of the membrane to water should be selected such that the flow rate through the membrane rather than the permeability of the skin is the predominant factor in establishing the flow rate into the patch.

The total flux into the collection patch is given by the relationship:

$$\frac{1}{J_T} = \frac{1}{J_P} + \frac{1}{J_S} \qquad (2)$$

where $J_T$ is the volumetric flow rate into the patch and $J_P$ and $J_S$ are the flow rates through the semipermeable membrane and the skin respectively.

Since $J_S$ is known $J_P$ can be selected according to Equation 1 to provide the appropriate degree of control desired for a particular system. Thus while considerable design flexibility exists, it is considered preferable to minimize the effect of deviations in $J_S$ by selecting $J_P$ to be no greater than $J_S/2$.

Since, in this embodiment, the membrane 4 will be in contact with the skin, it should be non-irritating which is not a significant problem since most of the semipermeable membranes known to the art are relatively inert and non-irritating. Simple screening, however, can be used to evaluate the materials or materials which are approved by the Food & Drug Administration for contact with the skin such as cellulose esters, including cellulose acetate and ethylcellulose, ethylene/vinyl acetate copolymers, polycarbonates and polysulfones optionally containing flux enhancers, for example can be used.

Figure 2:
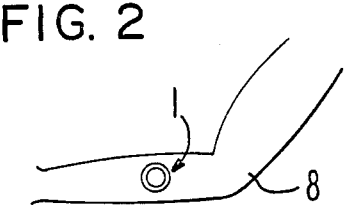
FIG. 2 shows a typical manner of application of a sweat collection patch according to this invention.

In use, the strippable liner 7 would be removed from the patch and the patch applied to a predetermined convenient site on the body such as the forearm, chest, under the arms, stomach, under the feet or any other suitable location as shown in FIG. 2 or on the gums, internal surface of the cheeks, the vagina or the like and maintained in place for a predetermined period of time. The site selected should minimize temperature variations. For this and cosmetic reasons a site normally covered by clothing or within a readily accessible body cavity is preferred. The particular time period selected will in most cases depend upon the substance, the presence of which is being detected, and the purpose for which the patch is being employed. Thus for example, if the patch is being used to quantify the amount of alcohol in the subject's sweat, a relatively short period of time such as an hour may be selected in view of both the relatively short half life of the drug in the body and the requirement to rapidly quantify the level in the sweat. On the other hand, if the purpose is merely to detect the presence of alcohol in any particular period of time such as for example, to determine whether airline pilots are complying with the requirement that they refrain from consuming alcoholic beverages for a predetermined period of time prior to flight, a longer selection period such as 24 or 48 hours can be utilized. After the expiration of the predetermined time period, the patch would be removed from the subject, the absorbent pad 3 removed and subject to standard analytical chemical tests to determine the presence and the amount of the substance that is being monitored. The result of this analysis will yield a time-integrated measure of the average concentration of the substance in the sweat during the collection period.

Figure 3:
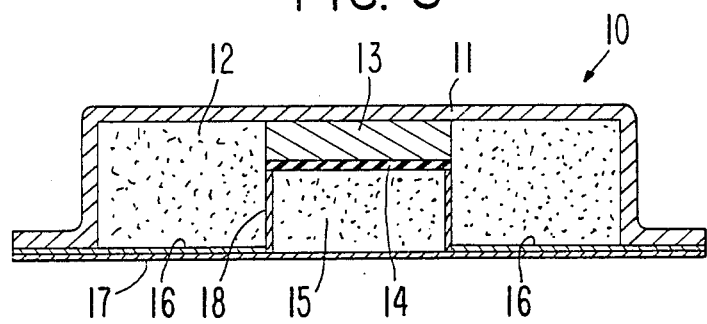
FIG. 3 is a cross-section through another embodiment of collection patch according to this invention.

Referring now to FIG. 3, another embodiment of skin patch 10 of this invention is shown which is capable of collecting materials which are impermeable to the rate controlling membrane. The principle of operation of patch 10 is basically the same as that of the embodiment of patch 1, except that the collecting pad 15 is placed between the skin and the semipermeable rate controlling membrane 14. This embodiment of the invention consists of a protective, preferably impermeable backing member 11 receiving an open-pore foam pad 12, typically circular in configuration, which is provided with a central receptacle within which is received a disc of osmotic agent 13, a rate controlling semipermeable membrane 14, a porous, fibrous or the like agent collecting member 15 which preferably contains dispersed activated charcoal, ion exchange resins, cross linked dextrans or other material, having the property of binding to the agent to be collected to separate it from the sweat flowing through member 15 and into the osmotic agent 13. An impermeable barrier which may be in the form of a sleeve 18 separates the collecting pad 15 from the porous pad 12. Sufficient osmotic agent is provided to maintain the concentration of the solution formed upon imbibition of water through rate-controlling semipermeable membrane 14 at the saturation level during the intended period of use. A contact adhesive 16, preferably impermeable to water is applied to the body contacting surfaces of the porous pad 12 and the base is covered with strippable protective liner 17.

The operation of patch 10 is basically similar to that of patch 1 except that the agent to be detected in the sweat is extracted from the sweat before fluid passes through the rate controlling semipermeable membrane 14. Also, the collecting pad 15 and the osmotic agent 13 are separated in patch 10, instead of combined as in patch 1 and the foam pad 12 provides a void volume into which water imbibed through the semipermeable membrane 14 can flow. Collection pad 15 can optionally have a microporous membrane separating pad 15 from the skin.

After the skin patch has been applied for the predetermined period of time, the patch would be removed, collection pad 15 separated from the patch 10 and subjected to analysis for the substance or substances to be detected according to standard analytical techniques known to the art for each particular substance.

It should be noted that pad 15 in FIG. 3 and/or contact adhesive 6 underlying the membrane 4 in FIG. 1 can contain an amount of a material such as dimethylsulfoxide, n-laurylsulphate, n-decyl methylsulfoxide (nDMS) or any other substance which is capable of increasing the permeability of the skin to water. Thus by substantially increasing the ambient flux of fluid through the skin in the vicinity of the collection patch, the rate controlling membranes 4 and 14 are permitted to perform their rate controlling function with a wider range of variation in skin permeability than is found in the normal population of potential users. As can be seen from the Baker, et al. supra, the application of a permeation enhancer such as sodium lauryl sulfate can increase the permeability of skin to water by approximately a factor of 2, thus permitting the skin patch to function as intended over a range of skin permeabilities greater than can be expected in the population at large.

Figure 4:
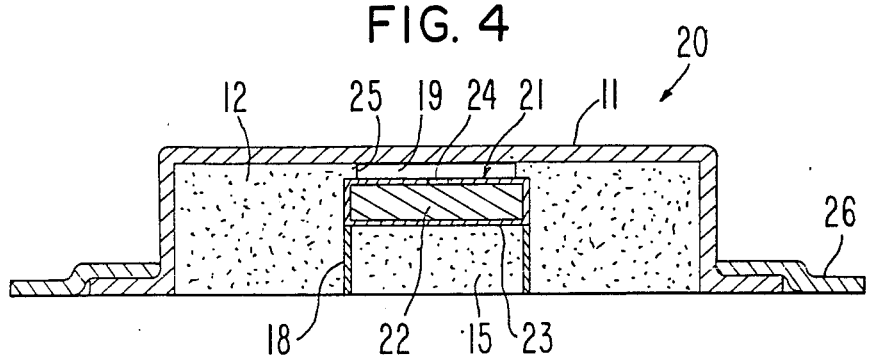
FIG. 4 is a cross-section through another embodiment of collection patch according to this invention.

Referring now to FIG. 4, another embodiment of the invention is shown in which the rate controlling membrane and osmotic agent are prefabricated into the form of an osmotic pump such as described in the aforementioned patents. Skin patch 20 according to this invention is similar to the embodiment of FIG. 3 except that the rate controlling membrane 23 and the osmotic agent 22 are preassembled in the form of an elementary osmotic pump 21 consisting of a core 22, comprising the osmotic agent surrounded by a semipermeable rate controlling membrane 23 and provided with a suitable outlet such as port 24 through which the solution formed within the pump by the imbibition of water from the skin can be vented. The patch itself consists of a protective backing 11 and a foam pad provided with a central receptacle, lined with impermeable sleeve 18, which in this case is also provided with an internal shoulder 25 which serves to space the outlet 24 of the pump 21 from the backing 11 to provide a fluid flow path through space 19, for the discharge of fluid from the pump 21 to the foam pad 12. The collecting pad 15 and sleeve 18 are essentially the same as that shown in FIG. 3. In FIG. 4 a separate adhesive overlay 26 in the form of an annular ring is used to hold the patch on the skin, eliminating the need for adhesive layer 16 and strippable layer 17. The embodiment of FIG. 4 is particularly advantageous since it facilitates the assembly of the device and also permits the selling of the device in unassembled kit form by which various osmotic pumps 21 and collecting pads 15, selected for their individual characteristics for detecting specific chemical agents could be provided and then assembled immediately prior to use. The patch 20 could be a universal design usable with a variety of osmotic pumps 21 and collecting pads 15 and this embodiment eliminates the need to separately handle the rate controlling membrane 14. These membranes are normally quite thin and unnecessary handling of the unsupported membrane which could damage or otherwise effect its permeability is thereby avoided.

The particular overall size of the patch is not critical and it is contemplated that the size of the collecting pad would be selected to provide a reasonable quantity of agent to be collected during the time of the collection period. The following examples indicate various embodiments of this invention for detecting representative substances.

EXAMPLE 1

A collection patch is fabricated from an open pore structured semi-rigid celluose based foam pad impregnated with potassium sulfate. A 10cm$^2$ disc (radius 1.8 cm) of the salt impregnated pad is placed into a plastic cup of 1.8 cm radius with flanged edges constructed of water impermeable polycarbonate. A 3 mil thick film of cellulose acetate butyrate 500-1 is cast and punched to 2 cm radius. The disc of semipermeable membrane is adhered by a silicone transfer adhesive to the flanges of the cup slightly compressing the salt impregnated pad, so as to effect a hydrostatically intact seal of the cup. The thus formed collection chamber is inserted through the center of an annular ring of Microfoam ® adhesive overlay. The collection patches with adhesive are placed on the skin at the inside and outside of the forearm below and above the elbow for determining the collection rate over time. FIG. 5 shows the experimental data expressed as volume rate of sweat collection versus residence time.

As reported by Philips et al: A Sweat Patch Test for Alcohol Consumption: Evaluation in Continuous and Episodic Drinker (Alcoholism: Chemical and Experimental Research 4(4) OCT, 1980), the correlation between alcohol levels in sweat and blood is represented by the equation:

$$ln C_s = 0.80\ ln C_b - 1.40$$

where $C_b$ and $C_s$ are mean concentrations, respectively of alcohol, in blood and sweat. For a mean blood alcohol level of 0.1% which corresponds to a daily intake of between 2-3 grams of whiskey per kg per day, the concentration of alcohol in sweat is 0.25 $\mu g/\mu l$. For the 10 cm$^2$ collection patch fabricated above and worn for 72 hours the cumulative amount of alcohol collected on a time integrated basis is 26 $\mu g$. The analysis of alcohol content in the salt impregnated pad is performed by head space gas chromatography.

EXAMPLE 2

A collection patch is fabricated from an annular ring of a cellulose-base, open-pore, semi-rigid foam pad arch punched with a 1.8 cm radius die leaving 0.1 cm thickness unpunched. A 1.7 cm radius arch punch is subsequently centered and a 1.7 cm radius hole is then formed through the remaining 0.1 cm thickness leaving a shoulder upon which the elementary osmotic pump tablet described below rests. A 15 mil thick, 3.6 cm outside diameter cylinder of polycarbonate is inserted into the 3.6 cm diameter well so as to rest against the shoulder of the foam pad and fit flush with the underside of the foam pad. A 1 ⅜ inch diameter disc of sodium chloride with polyethylene oxide binder in the ratio of 85:15 is tableted and coated with a rate controlling membrane of polymethyl methylacrylate and cellulose acetate butyrate 500-1 in the ratio of 25:75 (by weight). A 20 mil exit port is drilled on one side of the membrane coated tablet to form an elementary osmotic pump and then inserted, exit port upwards, into the polycarbonate well until the coated disc rests against the shoulder of the foam pad. Scotchpak ® polyester metalized film is adhered to the upper face and side of the annular foam pad with Densil ® transfer adhesive to effect a hydrostatic seal. A collection disc of cellulose-base foam pad of 3.5 cm diameter is inserted into the well beneath the coated salt disc. A hydrophobic pressure sensitive adhesive is applied to the underside of the annular ring of foam pad to adhering the patch to the skin. The collection patch is tested in vitro and in vivo at 32° C. and the volume rate of imbibition is 0.65 $\mu l/hr/cm^2$.

Antipyrine is delivered rectally to a subject from a controlled release dosage form that provides approximately 15 mg/hr antipyrine input at a steady rate for 30 hours. At 30 hours and 60 hours, the spent systems are removed and replaced so that steady state plasma levels are maintained for 90 hours at 5 $\mu g/ml$. Three collection patches as fabricated above are worn on the inside of the forearm. At 30 hour intervals up to 90 hours the collection patches are removed and a time-integrated measure of antipyrine in the collection discs of foam pad are determined by the method of Brodie. Results at 30, 60, and 90 hours are 0.73 $\mu g$, 1.8 $\mu g$, and 2.9 $\mu g$ antipyrine. Since the collection rate is rated at 0.65 μl/hr/cm², the time-integrated measure of antipyrine in the collection patch indicates an average plasma concentration of 5 μg/ml.

EXAMPLE 3

A collection patch is fabricated identical to example 2 above except the cellulose-base foam pad collection disc is impregnated with activated charcoal sufficient in quantity to bind 100 μg of theophylline.

Theophylline as cholinetheophyllinate is delivered rectally by means of a controlled release, rectal osmotic dosage form designed to deliver theophylline at a constant rate of 11 mg/hr for 36 hours. At 36 hours the spent dosage form is replaced with another until 72 hours is reached at which time dosing is terminated. Steady state plasma levels are measured to be approximately 3 μg/ml. Two collection patches are placed on the inside forearm at the beginning of the study and one is removed at 36 hours and the other at 72 hours. Theophylline content as measured by chromatographic assay of the collection disc is determined to be 0.36 μg at 36 hours and 0.83 μg at 72 hours. Since the volume rate of collection is 0.65 μl/hr/cm² the time integrated measure of theophylline content indicates an average plasma concentration of 3 μg/μl knowing that the relationship between theophylline plasma concentration and theophylline sweat concentration is $C_s = 0.67\ C_p$.

Having thus generally described our invention it will be readily apparent that various modifications can be made by workers skilled in the art without departing from the scope of this invention which is limited only by the following claims wherein:

We claim:

1. A fluid collection patch to be placed on the body surface of a subject for determining the presence of an agent in the fluid collected from said body surface during a fluid collection period comprising, in combination:
    (a) receptacle means;
    (b) agent collection means within said receptacle means for collecting the agent to be detected during the collection period, said agent collection means being adjacent to said body surface;
    (c) rate controlling means for maintaining the rate at which body fluid flows through said agent collection means over a substantial portion of said collection period at a substantially constant level below the rate at which body fluid is secreted at the body surface at the collection site, wherein said rate controlling means comprises (i) an osmotic pressure generating solute and (ii) a semipermeable membrane disposed between said solute and said agent collection means, where said agent collection means is disposed in the path of fluid flow between said membrane and said body surface, and said osmotic solute being present in an amount sufficient to maintain the solution produced by osmotic imbibition of water through said semipermeable membrane at the saturation level during the collection period, and said membrane being impermeable to the agent to be collected; and
    (d) means for maintaining said agent collection means in fluid transmitting relationship with said body surface during said collection period.

2. The patch of claim 1 further comprising means for increasing the rate at which fluid is secreted through the body surface at the collection site.

3. The patch of claim 1 wherein said fluid is sweat and said body surface is skin.

4. The patch of claim 1 wherein said fluid is secreted through a mucous membrane and said body surface is a mucous membrane.

5. The collection patch of claim 1 further comprising agent binding means in said collecting means.

6. A fluid collection patch to be placed on a body surface of a subject for determining the presence of an agent in the fluid collected from said body surface during a fluid collection period comprising, in combination:
    (a) receptacle means;
    (b) agent collection means within said receptacle means for collecting the agent to be detected during the collection period;
    (c) rate controlling means for maintaining the rate at which body fluid flows into said agent collection means over a substantial portion of said collection period at a substantially constant level below the rate at which body fluid is secreted at the body surface at the collection site, wherein said rate controlling means comprises (i) an osmotic pressure generating solute and (ii) a semipermeable membrane disposed between said solute and said body surface, said osmotic solute being present in an amount sufficient to maintain the solution produced by osmotic imbibition of water through said semipermeable membrane at the saturation level during the collection period, and said membrane being permeable to the agent to be collected; and
    (d) means for maintaining said agent collection means in fluid transmitting relationship with said body surface during said collection period.

7. The patch of claim 6 further comprising means for increasing the rate at which fluid is secreted through the body surface at the collection site.

8. The patch of claim 6 wherein said fluid is sweat and said body surface is skin.

9. The patch of claim 6 wherein said fluid is secreted through a mucous membrane and said body surface is a mucous membrane.

10. The collection patch of claim 6 wherein said solute is dispersed through said agent collection means.

11. A fluid collection patch to be applied to a body surface of a subject for determining the presence of an agent in the fluid collected from said body surface during a collection period, comprising:
    (a) a fluid impermeable backing member forming a generally concave receptacle open at its body proximal portion;
    (b) agent collecting means received within at least a portion of said backing means, said collecting means having a body proximal surface and a body distal surface, the body proximal surface of said collecting means being adapted to be maintained in fluid conducting relationship to the body surface to which the patch is applied;
    (c) an osmotic solute within said receptacle, said solute being soluble in the fluid to be collected and present in an amount sufficient to maintain the solution thereof with the fluid to be collected at the saturation level during the collection period;
    (d) a semipermeable membrane impermeable to the agent being collected, and disposed between said collecting means and said osmotic solute, where said osmotic solute is disposed between said membrane and said backing such that fluid reaching said osmotic solute must flow through said semipermeable membrane, the thickness of said semipermeable membrane being sufficient to maintain the flow rate of fluid from said body surface to said osmotic solute at a rate below that at which said fluid is produced at said body surface; and (e) means for maintaining said patch on said body surface during the collection period.

12. The patch of claim 11 further comprising a porous fluid receiving member filling a substantial portion of the remainder of said receptacle and positioned between said agent collecting means and said backing member, and a fluid impermeable means adjacent to said pad and enclosing the side surfaces of said collecting means.

13. The patch of claim 12 further comprising agent binding means in said collecting means.

14. The patch of claim 12 further comprising means for increasing the water permeability of the body surface to which the patch is applied.

15. The collection patch of claim 12 further comprising:

said solute and semipermeable membrane formed into an elementary osmotic pump maintained in juxtaposition to said agent collecting means and said elementary osmotic pump having an agent collecting means proximal side and an agent collecting means distal side, the outlet of said pump being positioned on the agent collecting means distal side of said elementary osmotic pump and discharging into said porous fluid receiving member.

16. A fluid collection patch to be placed on a body surface of a subject for determining the presence of an agent in the fluid collected during a fluid collection period comprising, in combination:

(a) agent collecting means;
(b) water impermeable receptacle means receiving said collecting means, said receptacle means being adapted when applied to the body of the subject to permit fluid from the body to flow to said collecting means and prevent the escape of fluid from the patch;
(c) rate controlling means for controlling the flow of fluid from the body to the collecting means during the collection period, said rate controlling means comprising (i) an osmotic pressure generating solute dispersed through said collecting means and (ii) a semipermeable membrane permeable to the agent being collected, disposed in the path of fluid flow between said agent collecting means and said body surface, said osmotic solute being present in an amount sufficient to maintain the solution produced by osmotic imbibition of water through said semipermeable membrane at the saturation level during the collection period; and
(d) means for maintaining said agent collecting means in fluid transmitting relationship with said body surface during said collection period.

17. The collection patch of claim 16 wherein said means for maintaining said collection patch on the body surface comprises adhesive means bonding at least the periphery of said patch to the body surface.

18. The collection patch of claim 17 wherein said body surface is skin and said fluid is sweat.

19. The collection patch of claim 17 wherein said adhesive means is an adhesive overlay.

20. The collection patch of claim 17 wherein said adhesive means comprises an adhesive coating on at least a portion of the body proximal surface of said patch.

21. The collection patch of claim 16 further comprising means for increasing the water permeabilty of the body surface at the collection site.

22. A fluid collection patch to be applied to a body surface of a subject for determining the presence of an agent in the fluid collected from said body surface during a collection period, comprising:

(a) a fluid impermeable backing member forming a generally concave receptacle open at its body proximal portion;
(b) agent collecting means received within said backing means, said collecting means having a body proximal surface and a body distal surface, the body proximal surface of said collecting means being adapted to be maintained in fluid conducting relationship to the body surface to which the patch is applied;
(c) an osmotic solute dispersed through said collecting means, said solute being soluble in the fluid to be collected and present in an amount sufficient to maintain the solution thereof with the fluid to be collected at the saturation level during the collection period;
(d) a semipermeable membrane permeable to the agent being collected and disposed on the body proximal surface of said collecting means such that fluid reaching the osmotic solute contained within said collecting means must flow through said semipermeable membrane, the thickness of said semipermeable membrane being sufficient to maintain the flow rate of fluid from said body surface to said osmotic solute at a rate below that at which said fluid is produced at said body surface; and
(e) means for maintaining said patch on said body surface during the collection period.

23. The patch of claim 22 wherein said collecting means substantially fills said receptacle.

24. A fluid collection patch to be placed on a body surface of a subject for determining the presence of an agent in the fluid collected during a fluid collection period comprising, in combination:

(a) agent collecting means;
(b) water impermeable receptacle means receiving said collecting means, said receptacle means being adapted when applied to the body of the subject to permit fluid from the body to flow to said collecting means and prevent the escape of fluid from the patch;
(c) rate controlling means for controlling the flow of fluid from the body to the collecting means during the collection period, said rate controlling means comprising (i) an osmotic pressure generating solute and (ii) a semipermeable membrane impermeable to the agent being collected, disposed between said agent collecting means and said solute, said osmotic solute being present in an amount sufficient to maintain the solution produced by osmotic imbibition of water through said semipermeable membrane at the saturation level during the collection period; and
(d) means for maintaining said agent collecting means in fluid transmitting relationship with said body surface during said collection period.

25. The collection patch of claim 24 further comprising means for increasing the water permeability of the body surface at the site of collection.

26. The collection patch of claim 24 wherein said means for maintaining said collection patch on the body surface comprises adhesive means bonding at least the periphery of said patch to the body surface.

27. The collection patch of claim 26 wherein said adhesive means is an adhesive overlay.

28. The collection patch of claim 26 wherein said adhesive means comprises an adhesive coating on at least a portion of the body proximal surface of said patch.

29. The collection patch of claim 26 wherein said body surface is skin and said fluid is sweat.

* * * * *